(12) United States Patent
Naylor et al.

(10) Patent No.: US 7,729,517 B2
(45) Date of Patent: Jun. 1, 2010

(54) METHOD AND APPARATUS FOR TESTING FIBRES

(75) Inventors: Geoffrey Robert Stewart Naylor, Ocean Grove (AU); Mark Michael Purmalis, St Albans (AU)

(73) Assignee: Commonwealth Scientific and Industrial Research Organisation, Campbell (AU)

( * ) Notice: Subject to any disclaimer, the term of this patent is extended or adjusted under 35 U.S.C. 154(b) by 839 days.

(21) Appl. No.: 10/553,711

(22) PCT Filed: Apr. 16, 2004

(86) PCT No.: PCT/AU2004/000505

§ 371 (c)(1),
(2), (4) Date: Sep. 28, 2006

(87) PCT Pub. No.: WO2004/092677

PCT Pub. Date: Oct. 28, 2004

(65) Prior Publication Data

US 2007/0035720 A1 Feb. 15, 2007

(30) Foreign Application Priority Data

Apr. 17, 2003 (AU) ............................. 2003901910

(51) Int. Cl.
*G06K 9/00* (2006.01)
(52) U.S. Cl. ..................... 382/111; 382/106; 382/108; 382/141
(58) Field of Classification Search ................. 382/106, 382/108, 111, 141
See application file for complete search history.

(56) References Cited

U.S. PATENT DOCUMENTS

| 6,407,819 | B1 | 6/2002 | Kuratle |
| 6,741,726 | B1 * | 5/2004 | Nevel et al. ................. 382/111 |
| 2002/0054694 | A1 * | 5/2002 | Vachtsevanos et al. ...... 382/111 |
| 2002/0117274 | A1 | 8/2002 | Jang |

FOREIGN PATENT DOCUMENTS

| FR | 2 512 196 | 3/1986 |
| WO | WO 91/11705 | 8/1991 |
| WO | WO 01/20321 | 3/2001 |

OTHER PUBLICATIONS

Naylor. "Cotton Maturity and Fitness Measurement Using the Sirolan-Laserscan." *Prestent at the Beltwide Cotton Quality and Cotton Textile Processing Conference*. Jan. 2001. 6 pages.
Bai et al. "Method and system for measuring wool fiber fineness measurement." Derwent. Jul. 2002.

* cited by examiner

*Primary Examiner*—Tom Y Lu
(74) *Attorney, Agent, or Firm*—Merchant & Gould P.C.

(57) ABSTRACT

According to the present invention there is also provided an apparatus for estimating the fiber fineness of a known mass of fibers, the apparatus including: an image capturing device for capturing either i) all of the fibers selected for testing or ii) a fraction thereof, in one or more images; a computer capable of automatically determining the total length of fiber or fibers in the or each image; and a means for estimating the fiber fineness of the fibers using the total fiber length in the image(s).

53 Claims, 7 Drawing Sheets

METHOD AND APPARATUS FOR TESTING FIBRES

FIELD OF THE INVENTION

The present invention relates to a method and apparatus for estimating the linear density of fibres. The term linear density has the same meaning as the term fibre fineness and the two terms are used interchangeably throughout this patent specification In the situation in which cotton and cellulosic fibres are being tested, the fibre fineness estimation provided by the present invention may also be used in estimating the maturity of the fibres.

As will be explained in greater detail below, both the fibre fineness and maturity of cellulosic fibres are useful indicators of the properties of fibres.

BACKGROUND OF THE INVENTION

The dimensions of fibres and in particular the cross-sectional dimensions transverse to the length of fibres are of considerable interest in determining the quality of fibres. In the case of fibres with an approximately circular cross-section the fibre diameter can be used to provide this information. For fibres with non-circular cross sections, a useful measure of the transverse 'size' of a fibre is its weight per unit length which is also known as linear density or fibre fineness. Fibre fineness is used widely with synthetic fibres where a variety of cross-sectional shapes can be readily engineered.

Average fibre fineness can be measured directly using a technique known as the gravimetric technique and is described in standard texts such as 'Physical Properties of Textiles', $2^{nd}$ edition by W. E. Morton and J. W. S. Hearle. For a given sample:

$$\text{Average Fibre Fineness} = \frac{\text{(Total weight of fibre being tested)}}{\text{(Total length of fibre being tested)}} \qquad \text{[Equation 1]}$$

The gravimetric technique can be carried out by forming bundles of parallel fibres, cutting the bundles into known lengths, weighing the cut fibres, and then counting the number of fibres in the sample. The average fibre fineness of the fibres in the bundles is calculated as follows:

$$\text{Average Fibre Fineness} = \frac{\text{(Total weight of fibre being tested)}}{\text{(Length of fibres)} \times \text{(Total number of fibres)}} \qquad \text{[Equation 2]}$$

This direct approach when undertaken manually requires considerable skill, time and labour. This is compounded by two practical limitations. Firstly, when using conventional weighing balances, the requirement of a certain level of precision in the weight measurement generally defines a minimum weight leading to a large number of fibres to be counted. Secondly, due to the inherent variability in many textile fibre samples and the need to obtain a measurement representative of the whole sample, it is generally necessary for the sample to have a large number of fibres.

Numerous attempts have been made to devise alternative methods for measuring the quality of fibres. The most successful alternative has been the development of porous plug or air flow fineness tester. The underlying principle of this method is that the resistance to airflow through a randomised compressed plug of fibres of known mass provides an indication of size of the pores between the fibres and thus the surface area of the fibres. Based on a theoretical relationship between the measured airflow resistance and the surface area per unit volume of the fibre it is possible to estimate the fineness of the fibres. The theoretical relationship is based on the assumption that the fibres are solid and have regular cross sectional shape.

This airflow approach has been widely applied for testing cotton and provides a characteristic of the fibres known as the 'micronaire' value. However, cotton and other cellulosic fibres generally have a central lumen and have irregular cross sectional shapes which complicates the interpretation and usefulness of the 'micronaire' value.

In cotton and other cellulosic fibres, the lumen or hollow centre is a result of the growth pattern of the fibre: layers of cellulose are deposited on the inside of the thin primary cell wall. FIG. 1 attached at the back of this specification illustrates the cross section of a cotton fibre.

For fibres having the structure shown in FIG. 1, another important property effecting the quality of the fibres is the degree of thickening of the cell wall which is sometimes referred to as fibre maturity. Following the nomenclature first introduced in the text "The Fineness and Maturity of Cotton" by F. T. Pierce and E. Lord (1939), the degree of thickening or circularity $\theta$ is defined from a cross section of a fibre to be the ratio of the wall area A to the area of a perfect circle having the same perimeter P:

$$\theta = 4\pi A/P^2 \qquad \text{[Equation 3]}$$

The maturity value M of a fibre may be expressed as function of the degree of thickening as follows:

$$M = \theta/0.577 \qquad \text{[Equation 4]}$$

An empirical relationship between micronaire (Mic), fibre fineness(F) and maturity (M) was published in a journal article entitled "Airflow through Plugs of Textile Fibres Part II. The Micronaire test for cotton" by E. Lord in 1956. The empirical relationship is as follows:

$$F*M = 3.86*Mic^2 + 18.16*Mic + 13 \qquad \text{[Equation 5]}$$

Limitations of the micronaire value are readily apparent from Equation 5. In particular, micronaire is related to the product of fibre fineness and fibre maturity. As a result, a coarse immature sample of fibres and a finer more mature sample of fibres can both have the same micronaire value. Moreover an infinite set of fibre fineness and maturity values can provide the same micronaire value. In other words micronaire is not a comprehensive indicator of the quality of fibres.

One attempt at resolving this shortcoming of micronaire values was addressed by the so-called double compression airflow method. Specifically, rather than taking one airflow resistance measurement, the double compression airflow method involves taking measurements of two different compression ratios applied to the plug. The double compression airflow method is commercially available via at least two avenues namely, the Shirley fineness-maturity tester (FMT) and the ASTM test method D3818-1979.

An alternative method previously proposed by one of the inventors of the present invention was mentioned at the Beltwide Cotton Conference in 1999 and described in a paper entitled "Measuring Cotton Fineness Independently of Maturity Using the Sirolan Laserscan," by G. R. S. Naylor and J. Sambell. The aim of the method was to semi-automate the direct gravimetric method for determining fibre fineness. The method involved suspending fibre snippets of approximately 2 mm long in a very dilute concentration in a liquid transport medium and counting the snippets one by one as each fibre snippet passed an optical sensor in the measurement cell. This approach utilised an existing instrument called the Sirolan-Laserscan as the automatic counter. Whilst this approach was found to give satisfactory results technically, it was too slow to be viable commercially.

At the Beltwide Cotton Conference in 2001 a paper entitled "Cotton Maturity and Fitness Measurement using the Sirolan-Laserscan" by G. R. S. Naylor identified that the fibre fineness value and a micronaire value independently measured could be used with Equation 5 to provide the average fibre maturity.

In addition, International patent application PCT/CH91/00017 (WO91/11705) describes the approach whereby fibres are placed in a plane between a lighting source and receiving optics connected to a CCD sensor i.e. a digital camera. The image is then manually analysed.

Several other approaches have been explored for determining cotton fineness. However, in spite of considerable research effort over the last 50 years there is still a need for a commercially viable method and apparatus for testing fibre fineness.

SUMMARY OF THE INVENTION

According to the present invention there is provided a method for estimating the fibre fineness of a known mass of fibres selected for testing, the method including the steps of:

capturing either i) all of the fibres being tested in one or more images or ii) a fraction of the fibres being tested in one or more images;

determining the total length of the fibre or fibres in the or each image using automated computer image analysis; and estimating the fibre fineness of the fibres using the total fibre length in the image(s).

It will be appreciated that steps a) to c) may be carried out contiguously or disjunctively in which each step may be performed at different locations and at different times.

In the situation when the fibres being tested happen to be cotton or other cellulosic fibres, it is preferred that the method may also include estimating the average maturity value using the estimated fibre fineness from step c) and a predetermined micronaire value.

In particular, it is preferred that the average maturity value be calculated using Equation 5 set out above.

It is preferred that step a) be carried out using an image capturing device. For example, the image capturing device may be a digital camera or alike recording device.

In a situation in which all of the fibres selected for testing are captured in a single image or a series of images, step b) determines the total fibre length of all the fibres from the image(s). An advantage in this approach is that the length of the fibres can be determined by computer image analysis with only little or negligible error and the fibre fineness can be estimated using Equation 1 mentioned above. It is noted however that in a situation in which all of the fibres being tested happen to be captured by a series of images, care should be taken to avoid overestimating the length of the fibres due to image overlap. If necessary, a correction factor may be used to take into account the degree by which the images overlap.

However, it has been found that a satisfactory estimate of the fibre fineness can also be achieved by capturing only a fraction of all of the fibres in one or more images. An advantage provided by this finding is that it is not necessary to measure the total length of the fibres selected for testing or to count the total number of fibres being tested in accordance with the prior art gravimetric technique described above.

In addition, unlike the prior art gravimetric technique in which there is a temptation to reduce the total number of fibres being tested and thus the weight of the fibres to a point were the capacity of the weighing balance may become influential in the accuracy of the fibre fineness estimation, the total mass of fibres being tested according to the present invention can be readily increased due to at least two factors. Firstly, automated computer image analysis is capable of determining the fibre length appearing in the image(s) much quicker than manually counting each fibre. Secondly, the present invention can be carried out without capturing an image of all of the fibres selected for testing and thus the number of images captured is not restricted to the mass of the fibres being tested.

Irrespective of whether all of the fibres or only a fraction thereof are captured in one or more images, the image(s) may be captured by dispersing the fibres over a viewing platform and operating the image capturing device such that the device captures all or only a sample of the fibres on the viewing platform. Different samples of the fibres may be captured by moving the image capturing device relative to the fibres or by moving the viewing platform relative to the image capturing device. The viewing platform may be moveable relative to the image capturing device by means of a conveyor.

However, it is preferred that the image(s) of the fibres be captured when the fibres are suspended in a fluid. The fluid may be in the form of a liquid such as water or a gas.

It is preferred that the method also include forming a suspension of a known volume containing the fibres being tested.

It is preferred that the method include conveying the suspension past the image capturing device such that one or more images of the fibres in suspension can be captured.

It is preferred that the suspension is conveyed past the imaging device such that the suspension and fluid passes the image capturing device only once.

It is preferred that the suspension be contained in a closed loop that extends past the image capturing device so that the suspension can be recirculated through the closed loop while the image(s) are captured. An advantage provided by this preferred aspect is that the number of images captured of the fibres in suspension is not limited by the volume of the suspension.

It is preferred that the volume of the suspension captured in the or each image also be known.

It is preferred that the method also include the step of weighing the fibres selected for testing.

It is preferred that the fibre fineness of the fibres be estimated when a preselected condition has been satisfied.

It is preferred that the preselected condition be satisfied when the standard error of the mean value of measured fibre length per image is equal to or less than a preselected value.

The term "standard error" in this specification means the ratio of the standard deviation of the set of values captured to the square root of the number of values. The images utilised in determining the standard error may or may not include all of the images captured.

It is preferred that the standard error be continuously recalculated after the capture of each image or a group of images to provide a running value of the standard error which may then be continuously compared to the preselected value while the method is carried out.

It will be appreciated that, in general, statistically the standard error of the mean fibre length will reduce as the number of images increases, and correspondingly the accuracy of the fibre fineness estimation obtained by the present invention will increase.

Furthermore, upon the preselected condition being satisfied, it is not necessary to continue to carry out step a). In other words, the number of images captured may also be controlled by the comparison between the running value of the calculated standard error of the mean value of fibre length per image and a preselected required maximum value.

In the situation when the fibres being tested happen to be of a known uniform length, it is possible that step b) involves counting the number of fibres in the image(s) using the automated computer image analysis.

However, regardless of whether the fibres in the image(s) are of a uniform length, it is preferred that step b) involves measuring the total length of fibre appearing in the image(s). According to this preferred aspect of the invention it is not necessary for the computer imaging analysis to count the total number of fibres in the image(s).

When the images capture only a portion or fraction of the total fibres being tested, it is possible that estimating the fibre fineness according to step c) can be calculated by at least two equivalent approaches.

The first approach involves estimating the mass of fibre appearing in the image(s) and calculating the length of fibre and fibre fineness in each image captured and, in turn, estimating the fibre finess of the overall sample of fibres. In the situation where the fibre is uniformly mixed in a liquid suspension, the total mass of fibre appearing in the image(s) may be expressed as a function of the total mass of fibre in the sample multiplied by a ratio of the volume of the suspension appearing in the image(s) to the total volume of the suspension. The fibre fineness of each image is then determined as a ratio of the mass of fibre in the image(s) to the length of fibre in the image(s) determined by step b).

The second approach involves determining the length of fibre in the image(s), estimating the total length of fibre in the overall sample, and in turn, estimating the fibre fineness of the overall sample. An estimate of the total length of fibre in the image(s) can be determined by multiplying a mean length of the fibre determined in step b) by a ratio representing the total fibre in the sample to the average portion of fibre in the image(s). In the situation where the fibres are uniformly mixed in a liquid suspension, the ratio may be expressed as a function of the total volume of the suspension to the volume of the suspension captured in the image(s) which is then multiplied by the mean length of fibre in the image(s) captured.

It will be appreciated that both of the approaches described above may be conveniently summarized using the following formula:

$$F = \frac{mv}{VL} \quad \text{[Equation 6]}$$

where
F represents the average fibre fineness of the fibres in the images
m represents the total mass of the fibres selected for testing
V represents the total volume of the fluid suspension
v represents the volume of the suspension visible in one image
L represents the mean length of fibre in the images captured A potential source of error is if fibres overlap or appear to cross in the image(s) captured. In this case the computer image analysis might determine that the total fibre length is smaller than the true fibre length because the fibre length is measured only once at the region where the fibres overlap. The potential for this error to have an impact on the accuracy of the fibre fineness estimation increases with the concentration of fibre in the image(s). However, a reduction in fibre concentration will also reduce the degree to which the fibres in the image(s) provide a representative sample of the fibres being tested i.e. in the situation when a fraction of the fibres being tested is captured in the images, the number of images required will increase to achieve a satisfactory estimate of fibre fineness.

It is preferred that the fibre concentration appearing in the image(s) range up to 10.0 millimeters of fibre per square millimeter of image ($mm/mm^2$).

It is preferred that the fibre concentration in the image(s) ranges up to 2.0 $mm/mm^2$.

It is preferred that the fluid passageway include a chamber having a transparent wall and that the field of view of the image capturing device be directed at the transparent wall for capturing images of the fibres in the chamber.

It is preferred that the cross-sectional area of the chamber transverse to the direction of flow of the suspension through the chamber vary such that the concentration of fibres captured in the image(s) can be adjusted by moving the position of the field of view of the image capturing device along the chamber. In effect, changing the position of the field of view of the image capturing device changes the volume of suspension present in the field of view of the image capturing device and thus the degree to which the fibres overlap in the images.

It is preferred that the position of the image capturing device be automatically adjusted along the chamber depending on the fibre concentration appearing in the images.

It is preferred that a computer automatically determine the fibre concentration appearing in the image(s) and if needed, automatically operate a drive means for moving the image capturing device along the chamber to change the fibre concentration in the image(s).

It will be appreciated that the fibre concentration in the image(s) may also be adjusted by changing the total volume of the fluid in which the fibres are suspended or the mass of fibres suspended in the fluid.

When the fluid in which the fibres are suspended happens to be a liquid, it is preferred that the method include adding a wetting agent to the liquid to improve the degree by which the fibres are uniformly distributed in the suspension.

It is preferred that the wetting agent be a surfactant or an alcohol or similar.

It is preferred that the surfactant be a commercial cleaning detergent.

It is preferred that the surfactant be a non-ionic surfactant.

It is preferred that at least 0.01% by volume of surfactant be added to the suspension.

It is preferred that the method also include draining and rinsing the closed loop containing the suspension after the fibre fineness has been estimated to prevent a subsequent sample to be tested from being contaminated.

According to the present invention there is also provided an apparatus for estimating the fibre fineness of a known mass of fibres, the apparatus including:
an image capturing device for capturing either i) all of the fibres selected for testing or ii) a fraction thereof, in one or more images;
a computer capable of automatically determining the total length of fibre or fibres in the or each image; and
a means for estimating the fibre fineness of the fibres using the total fibre length in the image(s).

It is preferred that the means for estimating the fibre fineness be a computer such as the computer for determining the length of the fibres in the image(s).

It is preferred that the image capturing device be directly linked to the computer for determining the fibre length in the image(s).

The apparatus may also include a viewing platform on which the fibres can be dispersed for capturing images of the fibres. As described above with reference to the method of the present invention, the viewing platform and/or the image capturing device may be movable so that the field of view of the image capturing device may be directed at different segments of the fibres dispersed on the viewing platform.

However, it is preferred that the apparatus include a fluid passageway that extends through the field of view of the image capturing device such that when the fibres are suspended in a fluid, images of the fibres can be captured as the fluid is conveyed through the passageway.

It is preferred that the passageway be a closed loop for recirculating the fibres through the field of view of the image capturing device. A benefit provided by this preferred aspect of the apparatus is that the number of images that can be captured of the fibres is not limited by the volume of the fluid and that the fibres can be captured in more than one image if desired by recirculating the fluid.

It is preferred that the apparatus includes a control means for controlling the total volume of the suspension in the fluid passageway.

There are several alternative arrangements that are capable of controlling the volume of the suspension. For instance, the fluid passageway may be flow connected to a chamber having a moveable wall so that adjusting the position of the wall adjusts the volume of fluid in the chamber and thus the volume of the fluid passageway. Additional fluid is drawn from a reservoir and/or excess fluid is released through an overflow system. However, it is preferred that the control means includes the fluid passageway being flow connected to a head vessel, whereby maintaining the fluid level in the head vessel ensures that the fluid passageway contains a constant known volume of the suspension.

It is preferred that the fluid passageway extending through the field of view of the image capturing device be a chamber having an inlet and an outlet and a transparent wall so that the image capturing device can capture images of the fibres passing through the chamber, and the chamber being configured such that the volume of the suspension in the field of view of the image capturing device be known.

It is preferred that the cross-section of the chamber in a direction transverse to the direction of flow through the chamber be graduated such that the volume of fluid in the field of view of the image capturing device varies along the chamber.

It is preferred that the depth of the chamber in a direction transverse to the direction of flow through the chamber taper continuously between the inlet and outlet of the chamber. An advantage provided by this preferred aspect of the present invention is that effective concentration of fibre in the image can be varied by capturing images at different positions along the chamber.

It is also possible that the cross-sectional area of the chamber transverse to the direction of flow through the chamber can be varied by actual movement of one wall of the chamber relative to another wall. An example of this would be a bellows type arrangement.

In the situation in which the cross-section of the chamber in a direction transverse to the direction of the flow through the chamber is graduated, it is preferred that the position of the field of view of the image capturing device be moveable along the chamber so that the volume of suspension in the field of view can be varied.

It is preferred that the apparatus include a drive assembly for adjusting the position of the image capturing device relative to the chamber.

It is preferred that a computer for operating the drive assembly be programmed so that it be able to determine the volume of suspension passing the field of view of the image capturing device. One of the advantages provided by this preferred aspect is that in the situation when the images capture a fraction of the fibres being tested, the fibre fineness of the fibres being tested can be estimated mathematically using Equation 6 above.

The accuracy of the fibre fineness estimation is dependent on several factors including the degree to which fibres in the field of the view of the image capturing device overlap and the degree to which fibres in the images lie in a plane transverse to the plane of the image(s) captured. The impact of these factors and the accuracy of the estimation is a function of the fibre concentration in the images.

Accordingly, it is preferred that the computer for operating the drive assembly automatically operates the drive assembly and thereby adjusts the position of the image capturing device when the fibre concentration in the image fall outside a selected range.

It is preferred that the computer operate the drive assembly to prevent the fibre concentration falling outside the range of 0 to 10 mm of fibre per square mm of image.

It is preferred that the computer for operating the drive assembly be the computer for determining the fibre length in the images.

It is preferred that the image capturing device include a recording device that can record images in a digital format.

It is preferred that the image capturing device also include illuminating means to assist in the capture of images of the fibres.

It is preferred that the illuminating means include a light source positioned on the opposite side of the chamber to the recording device such that light is transmitted through the fibres can be detected by the recording device. An advantage provided by this arrangement is the specific arrangement commonly known as dark field illumination such that the background in the image can be darkened and the fibres brightened due to the detection of light being scattered while being transmitted through the fibres.

It is also preferred that the illuminating means include a light source on the same side of the chamber as the recording device such that light reflected from the fibres can be detected by the recording device.

It is preferred that the illuminating means be moveable relative to the chamber such that when the image capturing means is moved relative to the chamber, the illuminating means is able to remain in a relatively fixed position compared to the image capturing device.

It is preferred that the illuminating means be moveable by the drive assembly for moving the image capturing device.

BRIEF DESCRIPTION OF DRAWINGS

A preferred embodiment of the present invention will now be described with reference to the accompanying Figures, of which.

DETAILED DESCRIPTION OF A PREFERRED EMBODIMENT

Figure 1:
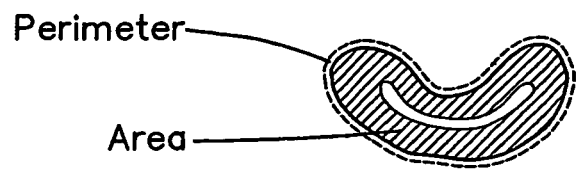
FIG. 1 illustrates the cross section of a cotton fibre.
Figure 2:
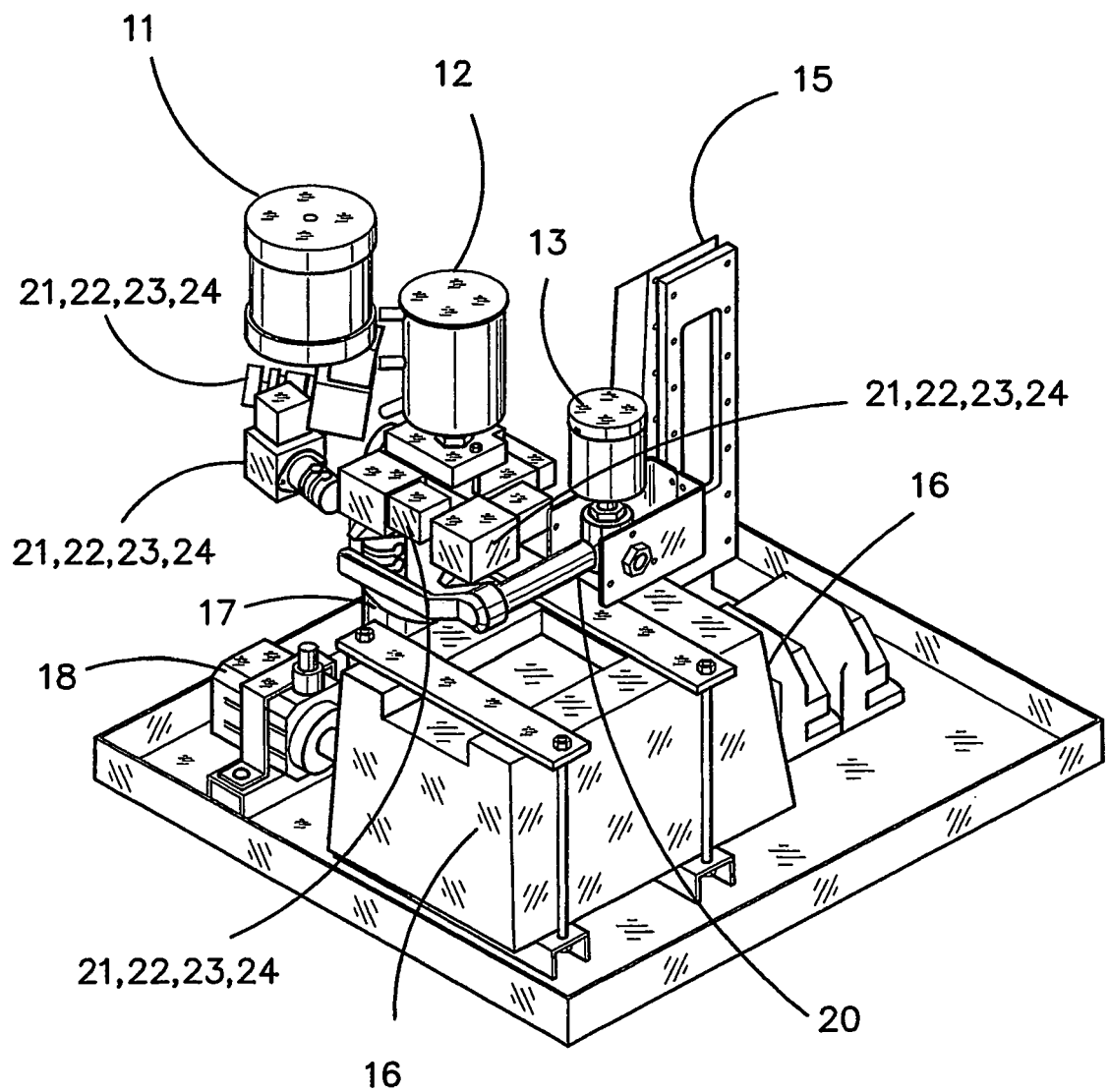
FIG. 2 is a perspective view of a partially assembled instrument for estimating fibre fineness.
Figure 3:
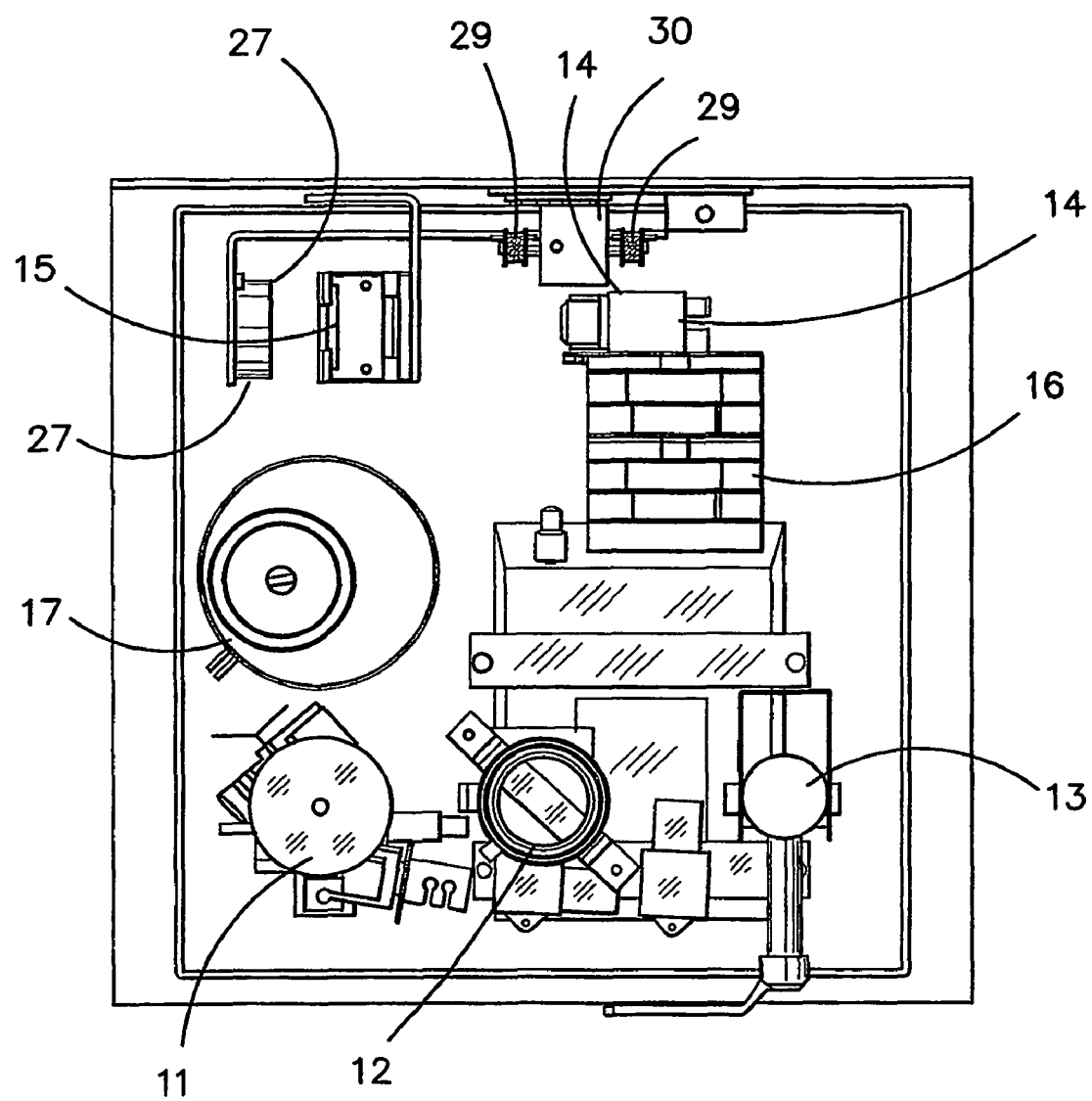
FIG. 3 is a top view of the partially assembled instrument illustrated in FIG. 2.

The instrument illustrated in FIGS. 2 and 3 includes the following equipment items: a head tank 11 containing water; a fibre sampling vessel 12 in which the fibres are mixed with water to form a suspension; a dispensing tank 13 for dispensing a known volume of water; an image capturing means in form of a digital camera 14; a flow cell 15 through which the suspension is conveyed; a peristatic pump 16 for pumping the suspension through the flow cell 15; a reservoir 17 for receiving the suspension upon completion of a test; and a pump 18 for pumping water from the reservoir 17 to the head tank 11.

Figure 8:
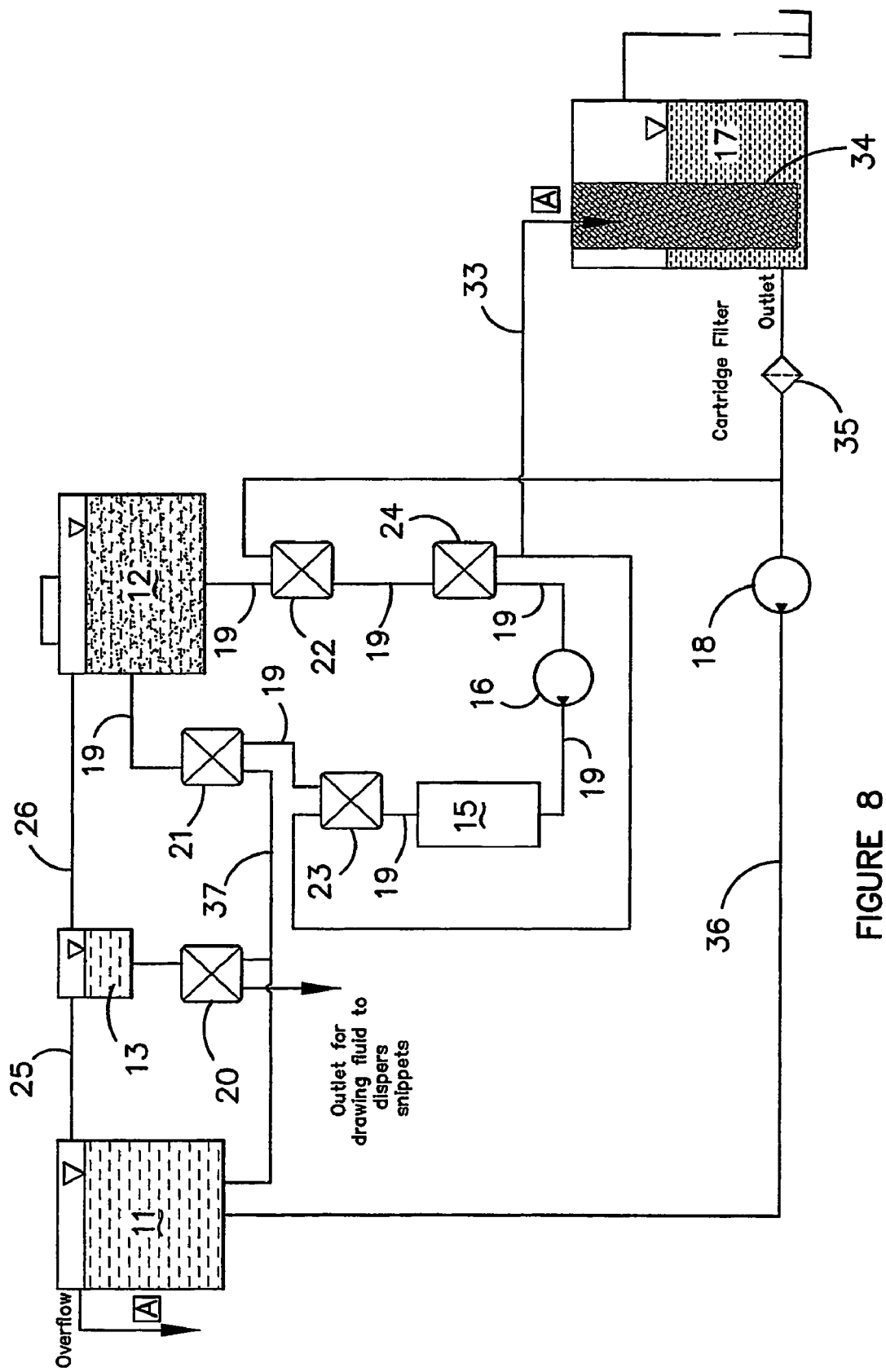
FIG. 8 is a piping flow diagram illustrating the piping and instrumentation interconnecting the equipment items shown in FIG. 2 to 7.

The equipment items are interconnected by piping and a series of control valves 21 to 24; the layout of the piping and control valves 21 to 24 is shown in detail in FIG. 8.

The piping generally identified by reference numeral 19 interconnects the flow cell 15 and the sampling vessel 12 to form a recirculating or closed loop so that fluid discharged from the sampling vessel 12 can be conveyed through the flow cell 15 and returned to the sampling vessel 12 continuously.

The instrument also includes equipment items such as a computer which is not shown in the Figures. The computer is linked to several equipment items of the instrument including the camera 14 and is capable of automatically determining the length of fibre in the images. The computer also operates the control valves 21 to 24 and pumps 16 and 18.

In order to estimate the fibre fineness of a sample of fibres, the fibres are firstly weighed and added to a beaker. They are then mixed together together with a known volume of water dispensed from the dispensing tank 13. As can be seen in FIG. 8, the dispensing tank 13 is flow connected to the head tank 11 by piping 19 so that the liquid level in the head tank 11 determines the amount of water dispensed from the dispensing tank 13 into the beaker.

The contents of the beaker is then emptied into the fibre sampling vessel 12 and mixed with additional water supplied from the head tank 11 to form a dilute suspension. The head tank 11 is flow connected to the sampling vessel 12 via piping 25 and 26 so that maintaining the liquid level in the head tank 11 ensures that the suspension formed in the recirculating loop defined in piping 19, sample vessel 12 and flow cell 15 contains a constant known volume.

Although not shown in the figures, the sampling vessel 12 also includes a mixing means for mixing the fibres and other material added to the sampling vessel 11 such as a surfactant. When the fibres being tested happen to be cotton, adding at least 0.01% by volume of a non-ionic short carbon chain surfactant improves uniformity of the distribution of fibres in suspension.

When the instrument is in use, the computer operates valves 21 to 24 and the peristatic pump 16 such that the suspension is conveyed continuously through the recirculating loop. The computer also operates the camera 14 so as to capture a series of images of the fibres passing through the flow cell 15.

Figure 4:
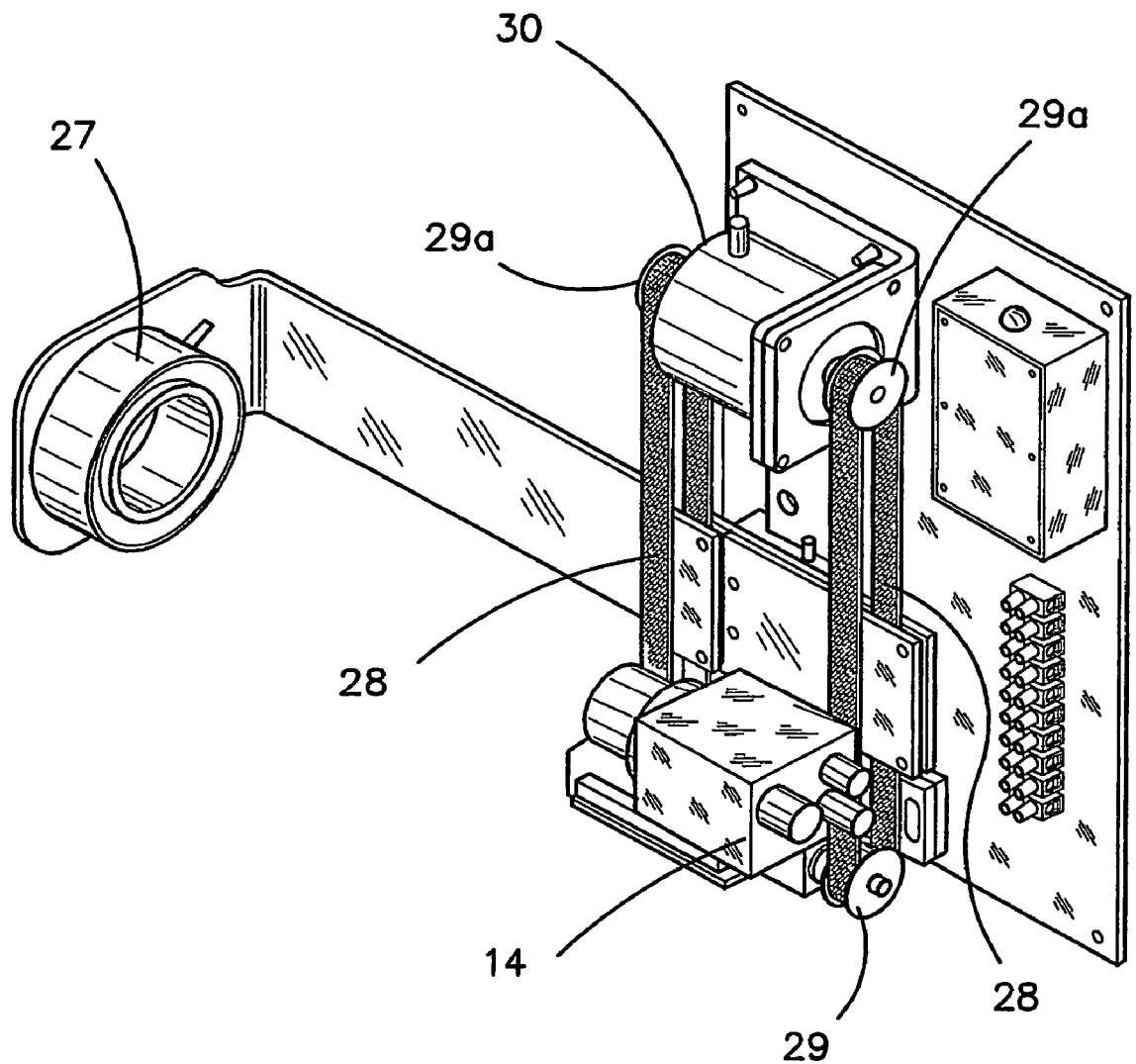
FIG. 4 is a detail view of a sub-assembly for capturing images of the fibres, this sub-assembly is not shown in FIG. 2.
Figure 5:
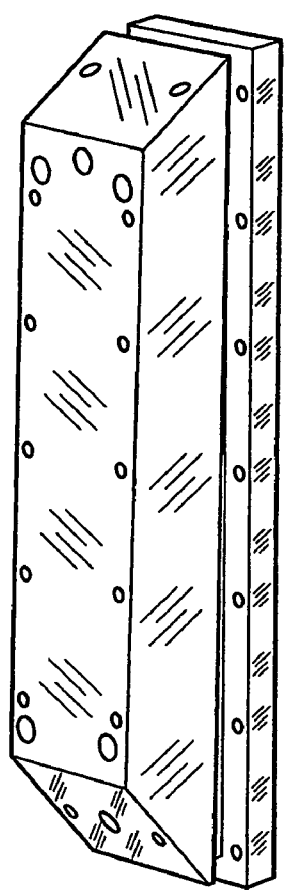
FIGS. 5 and 6 are perspective and front views respectively of a chamber through which the fibres are conveyed.
Figure 6:
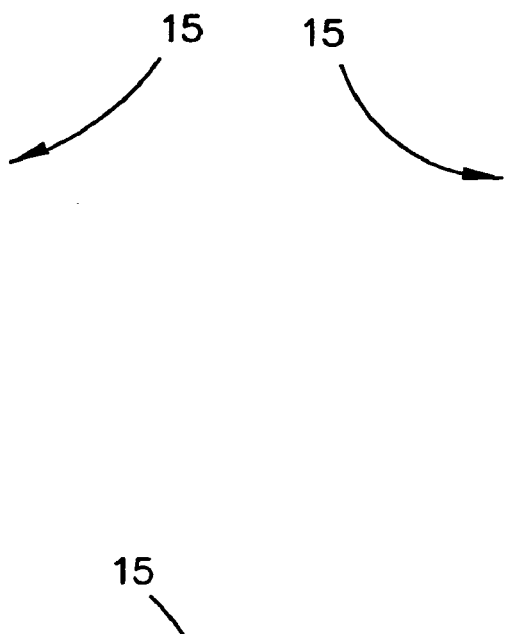
Figure 6:
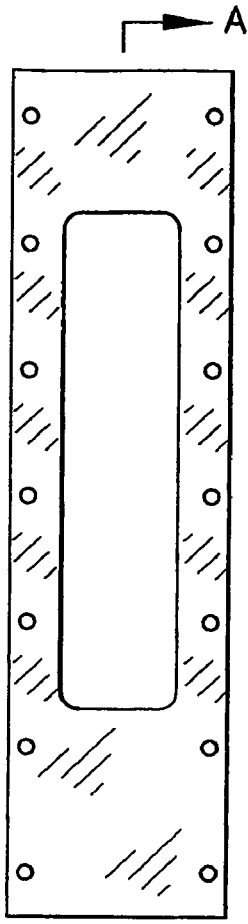

FIG. 4 illustrates in detail an assembly for capturing images of the fibres conducted through the flow cell 15. The assembly includes an illuminating means in the form of an annular light 27 and the digital camera 14. Both the digital camera 14 and the light 27 are moveable by way of a conveyor comprising two spatially separated belts 28 in which each belt 28 is held under tension in a vertical orientation between two pulleys 29. The upper pulley 29a is rotatably driven by a step-motor 30 which is operated and controlled by the computer so that the camera 14 and light 27 can be raised or lowered in increments.

The flow cell 15 is positioned between the camera 14 and the light 27. The flow cell 15 is a transparent chamber that allows the field of view of the camera 14 to be directed at and focussed on the suspension flowing through the flow cell 15.

Once the digital images of the fibres have been captured and fed to the computer, suitable algorithms stored in the computer enable it to determine the fibre length appearing in the images.

A typical assumption made in carrying out digital image analysis is that the objects appearing in each image, i.e. fibres, are located in a plane parallel to the plane of the image. A possible consequence of this assumption is that the image analysis may not take into account the fibre length in a plane transverse to the plane of the image or is obscured from view such as the length of a fibre overlapped by another fibre. The incidence of fibres overlapping increases with the concentration of fibres in an image.

In an attempt to balance these errors against the speed of operation, the flow cell 15 is designed to include a fluid passageway 31 that tapers between fitting 32 and fitting 33 such that the cross-sectional area of the fluid passageway 31 transverse to the direction of flow of the suspension through the passageway alters. This design allows the volume of suspension passing through the field of view of the camera and thus the concentration of fibre appearing in an image to be adjusted. In particular, the position of the camera 14 along the flow cell 15 has been calibrated with the computer so that the computer is able to assess whether the position of the camera 14 should be adjusted to reduce or increase the concentration of fibres appearing in the images. If needed, the computer can increase the concentration of fibres appearing in the image(s) by moving the camera 14 to a position in which the cross-sectional dimension of the fluid passageway 31 is greater. Conversely, if the fibre concentration in the image is too high, the computer can automatically reduce the concentration of fibre appearing in the image by moving the camera 14 to a position in which the cross-sectional dimensions of the fluid passageway is less.

It is recommended that the concentration in the image range from 0 to 10 millimeters of fibre per square millimeter of image.

According to the preferred embodiment the computer is also calibrated so that for each image captured, the computer can determine the volume of suspension passing through the field of view of the camera 14. Accordingly, in view of the head tank 11 maintaining the volume of suspension in the recirculating loop at a known volume, and the volume of suspension in each image also being known to the computer, the preferred embodiment is capable of estimating the fibre fineness of a sample of fibres using Equation 6 mentioned above.

An advantage provided by the preferred embodiment is that the fibres being tested may or may not have a uniform length and that it is not necessary to count the actual number of fibres being tested as is required by the prior art gravimetric technique.

According to the preferred embodiment, the fibre fineness is estimated (using Equation 6) when a preselected condition has been satisfied. Specifically, the preselected condition is satisfied when the difference between the mean length of fibre in the images captured(save for the last image captured) and the length of fibre in the last image captured is equal to or less than a maximum preselected value.

Figure 7:
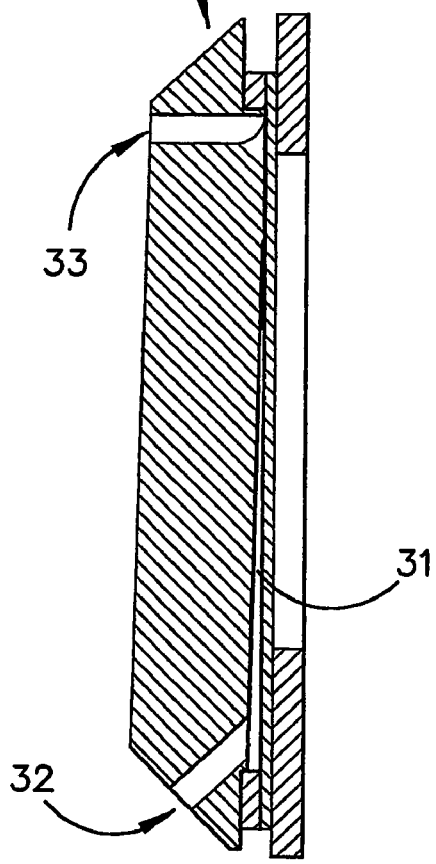
FIG. 7 is a cross-sectional view of the chamber along the line A to A in FIG. 6.

Upon the fibre fineness being estimated for a sample of fibres, the camera 14 ceases to capture further images and the computer automatically operates pumps 18 and 16 and control valves 22 and 24 in order to drain and rinse the recirculating loop so that a subsequent sample of fibres to be tested by the instrument is not contaminated. The draining cycle involves releasing the suspension from the recirculating loop through piping (there is an item 33 already in FIG. 7) into the reservoir 17. As can be seen in FIG. 8, the reservoir 17 includes a filter bag 34 and cartridge filter 35 for separating fibres from the water. Filtered water can then be returned to the head tank 11 via piping 36 so that the instrument can be operated for extended periods without supplying fresh water. The filter bag 34 and cartridge filter 35 can be removed from the reservoir 17 and cleaned on a routine basis or as needed.

Upon completion of the draining cycle, the recirculating loop and connected piping and control valves can be flushed with water supplied by the head tank 11 via pipe 37 to the sampling vessel 12 and through the recirculating loop. The water used for flushing is also discharged from the recirculating loop into the dispensing tank via piping 33.

A person skilled in the art would appreciate that many modifications may be made to the preferred embodiment without departing from the spirit and scope of the present invention.

Figure 9:
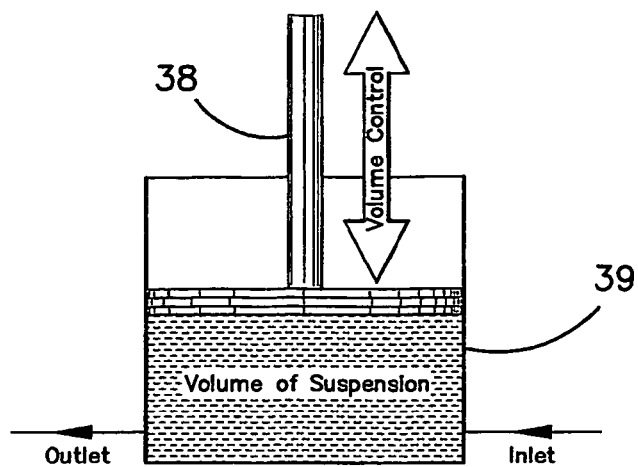
FIGS. 9 to 12 illustrate alternative mechanisms for controlling the total volume of fluid in the instrument.

For example, FIGS. 9 to 12 illustrate four alternative means for controlling the total volume of fluid suspension in the recirculating loop. Specifically, FIG. 9 shows an arrangement wherein the total volume is controlled by a piston 38 and cylinder 39 arrangement whereby the volume of the cylinder forming part of recirculation loop can be adjusted by movement of a piston 38. This embodiment suffers from the disadvantage that fibre may become caught or foul the seal between the piston 38 with the cylinder 39.

Figure 10:
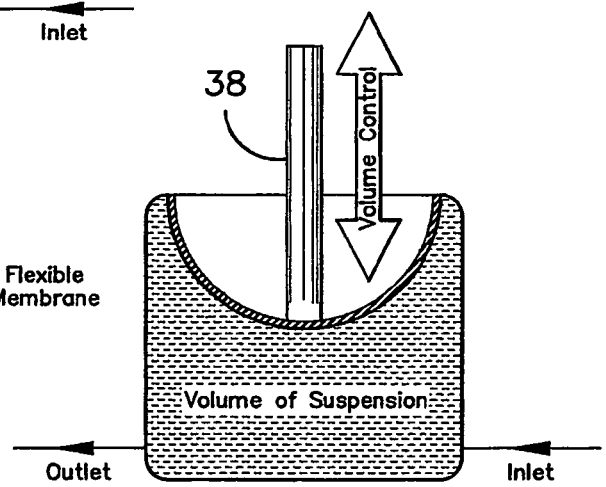

FIG. 10 shows an arrangement wherein the volume is controlled by means of a flexible membrane being stretched by a piston 38 so as to control the volume of the chamber forming part of the recirculating system. A problem with this arrangement is that the shape by which the membrane stretches may vary over time due to fatigue and moisture sorption.

Figure 11:
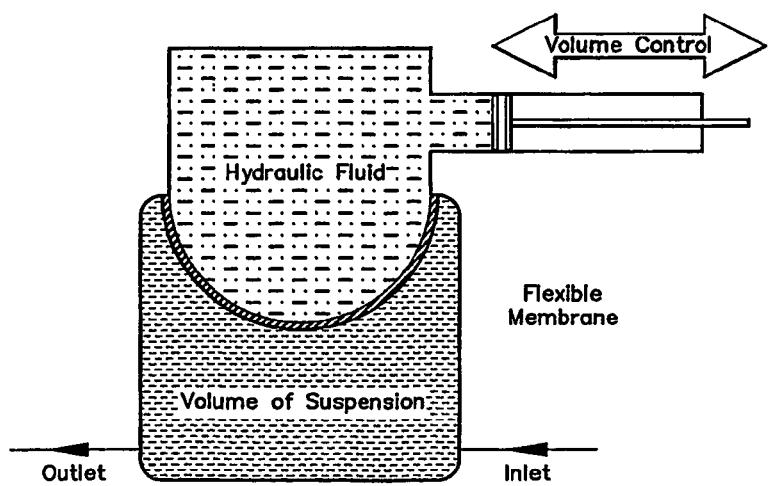

FIG. 11 illustrates an arrangement wherein volume is controlled by means of a flexible membrane in which a hydraulic fluid acts on one side of the membrane to adjust the volume of a chamber incorporated in the recirculating loop. The arrangement in FIG. 11 overcomes the difficulties with the arrangements shown in FIG. 9 and 10.

Figure 12:
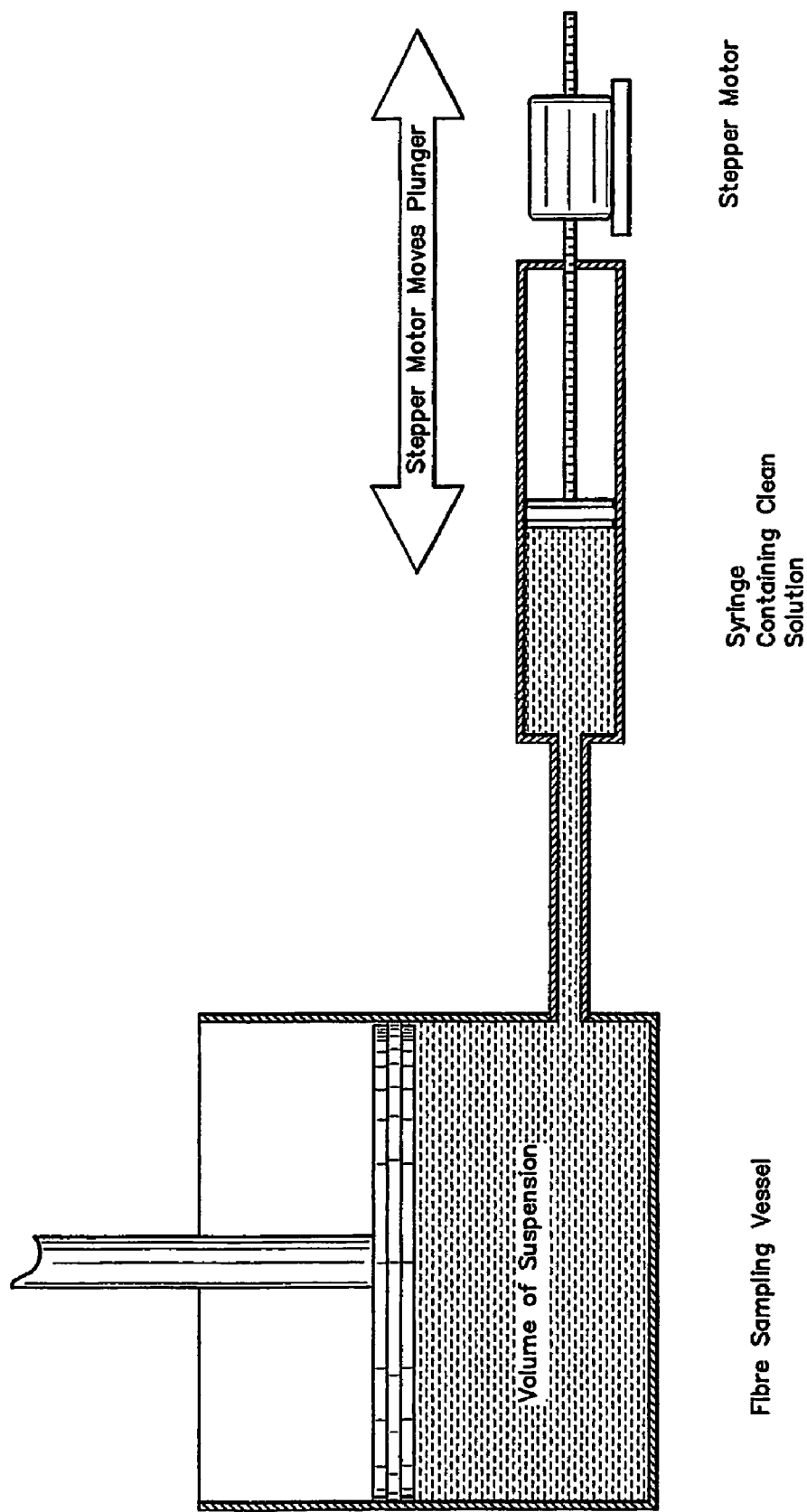

FIG. 12 illustrates yet another arrangement in which a piston and cylinder are flow connected to the fibre sampling vessel. A stepper motor or linear actuator operates the piston to deliver a precise amount of additional clean fluid from the cylinder into the sampling vessel and thereby further dilutes the suspension.

The claims defining the invention are as follows:

1. A method for estimating the fibre fineness of a known mass of fibres, the method including the steps of:
   a) capturing with an image capturing device either i) all of the fibres being tested in one or more images or ii) a fraction of the fibres being tested in one or more images;
   b) determining the total length of the fibre or fibres in the or each image using automated computer image analysis; and
   c) estimating the fibre fineness of the sample of fibres using the total fibre length in the image(s).

2. The method according to claim 1, wherein the method includes estimating the mass of fibre in the image(s) captured.

3. The method according to claim 2, wherein step c) involves dividing the mass of fibre estimation by the length of fibre determined in step b).

4. The method according to claim 2 whereby when step a) involves capturing a series of images that overlap, step b) involves taking into account the length of fibre in an overlapping section of the images to avoid over estimating the total length of fibre.

5. The method according to claim 2, wherein the image capturing device is a digital camera.

6. The method according to claim 2, wherein the sample of fibres is dispersed on a viewing platform and relative movement between the viewing platform and the image capturing device enables a series of images to be captured.

7. The method according to claim 2, wherein the fibres captured in the images are suspended in a fluid to form a suspension of known volume.

8. The method according to claim 7, wherein the method includes forming the suspension by mixing the fibres in a fluid.

9. The method according to claim 8, wherein estimating the mass of fibre in the image(s) is based on the volume of fluid in the field of view of the image capturing device compared to the total volume of the fluid in which the fibres are suspended.

10. The method according to claim 7, wherein the method includes conveying the suspension past the image capturing device such that one or more images of the fibres in the suspension can be captured.

11. The method according to claim 10, wherein the suspension is contained in a closed loop that extends past the image capturing device so that the suspension can be recirculated through the closed loop while the image(s) are captured.

12. The method according to claim 7, wherein a known volume of the suspension is in the field of view of the image capturing device and thus captured in the or each image.

13. The method according to claim 1, wherein the method also includes the step of weighing the sample of fibres selected for testing.

14. The method according to claim 1, wherein the fibre fineness of the fibres is estimated when the standard error of the mean value of measured fibre length per image determined in step b) is equal to or less than a preselected value.

15. The method according to claim 14, wherein the standard error be continuously recalculated after the capture of each image or a group of images to provide a running value of the standard error which may then be continuously compared to the preselected value while the method is carried out.

16. The method according to claim 15, whereby when the fibres being tested are of a known uniform length, step b) involves counting the number of fibres in the image(s) using the automated computer image analysis.

17. The method according to claim 7, wherein an estimate of the fibre fineness is calculated using the formula:

$$F = \frac{mv}{VL}$$

wherein
F represents the average fibre fineness of the fibres in the images;
m represents the total mass of the fibres selected for testing;
V represents the total volume of the fluid suspension;
v represents the volume of the suspension captured in each image; and
L represents the mean length of fibre in the images captured.

18. The method according to claim 7, wherein the fibre concentration appearing in the image(s) ranges up to 10.0 millimeters of fibre per square millimeter of image (mm/mm$^2$).

19. The method according to claim 18, wherein the fibre concentration in the image(s) ranges up to 2.0 mm/mm$^2$.

20. The method according claim 7, wherein the image capturing device includes a chamber through which the suspension is conveyed, the chamber having a transparent wall and the field of view of the image capturing device is directed at the transparent wall for capturing images of the fibres in the chamber.

21. The method according to claim 20, wherein the cross-sectional area of the chamber transverse to the direction of flow of the suspension through the chamber vary such that the concentration of fibres captured in the image(s) can be adjusted by moving the position of the field of view of the image capturing device along the chamber.

22. The method according to claim 21, wherein the image capturing device is automatically adjusted along the chamber depending on the fibre concentration appearing in the images.

23. The method according to claim 7, wherein the fibre concentration in the image(s) is adjusted by changing the total volume of the fluid in which the fibres are suspended or the mass of fibres suspended in the fluid.

24. The method according to claim 7, wherein when the fluid of the suspension is a liquid, the method further includes adding a wetting agent to the liquid to improve the degree by which the fibres are uniformly distributed in the suspension.

25. The method according to claim 24, wherein the wetting agent is a surfactant or an alcohol.

26. The method according to claim 24, wherein the surfactant is a commercial cleaning detergent.

27. The method according to claim 24, wherein the surfactant is a non-ionic surfactant.

28. The method according to claim 1, whereby when the fibres being tested are cotton or other cellulosic fibres, the method also includes estimating the average maturity value using the estimated fibre fineness from step c) and a micronaire value for the sample of fibres.

29. The method according to claim 27, whereby the average maturity value is calculated by the following equation:

$F*M = 3.86*Mic^2 + 18.16*Mic + 13$ wherein F is fibre fineness estimated in step c), M is maturity and Mic is micronaire.

30. An apparatus for estimating the fibre fineness of a known mass of fibres, the apparatus including:
an image capturing device for capturing either i) all of the fibres selected for testing or ii) a fraction thereof, in one or more images;
a computer capable of automatically determining the total length of fibre or fibres in the or each image; and a means for estimating the fibre fineness of the fibres using the total fibre length in the image(s).

31. The apparatus according to claim 30, wherein the means for estimating the fibre fineness is a computer that can i) estimate the mass of fibre in the image(s) captured and ii) divide the mass estimate by the length of fibre in the image(s).

32. The apparatus according to claim 31, wherein when the image capturing device captures image(s) of the fibres suspended in a substantially uniform fluid suspension, the computer estimates the mass of fibre in the image(s) based on the volume of fluid in the field of view of the image capturing device compared to the total volume of the fluid in which the fibres are suspended.

33. The apparatus according to claim 32, wherein the computer is programmed to estimate the fibre fineness using the formula:

$$F = \frac{mv}{VL}$$

wherein
F represents the average fibre fineness of the fibres in the images;
m represents the total mass of the fibres selected for testing;
V represents the total volume of the fluid suspension;
v represents the volume of the suspension captured by each image; and
L represents the mean length of fibre in the images captured.

34. The apparatus according to claim 30, wherein the image capturing device is directly linked to the computer for determining the fibre length in the image(s).

35. The apparatus according to claim 30, wherein the apparatus includes a fluid passageway that extends through a field of view of the image capturing device such that when the fibres are suspended in a fluid, images of the fibres can be captured as the fluid is conveyed through the passageway.

36. The apparatus according to claim 35, wherein the passageway is in the form of a closed loop for recirculating the fibres through the field of view of the image capturing device.

37. The apparatus according to claim 36, wherein the apparatus includes a control means for controlling the total volume of the suspension in the fluid passageway.

38. The apparatus according to claim 37, wherein the control means is provided by the fluid passageway being flow connected to a head vessel, whereby maintaining the fluid level in the head vessel ensures that the fluid passageway contains a constant known volume of the suspension.

39. The apparatus according to claim 38, wherein the fluid passageway includes a chamber that extends through the field of view of the image capturing device including a transparent wall so that the image capturing device can capture images of the fibres passing through the chamber, and the chamber is configured such that the volume of the suspension in the field of view of the image capturing device is known.

40. The apparatus according to claim 38, wherein the cross-section of the chamber in a direction transverse to the direction of flow through the chamber is graduated such that the volume of fluid in the field of view of the image capturing device varies along the chamber.

41. The apparatus according to claim 40, wherein the depth of the chamber in a direction transverse to the direction of flow through the chamber tapers continuously between the inlet and outlet of the chamber.

42. The apparatus according to claim 40, wherein the cross-sectional area of the chamber transverse to the direction of flow through the chamber can be varied by actual movement of one wall of the chamber relative to another wall.

43. The apparatus according to claim 40, wherein the position of the field of view of the image capturing device is moveable along the chamber so that the volume of suspension in the field of view can be varied.

44. The apparatus according to claim 43, wherein the apparatus includes a drive assembly for adjusting the position of the image capturing device relative to the chamber.

45. The apparatus according to claim 44, wherein a computer for operating the drive assembly is programmed so that it can determine the volume of suspension passing the field of view of the image capturing device.

46. The apparatus according to claim 44, wherein the computer for operating the drive assembly automatically operates the drive assembly and thereby adjusts the position of the image capturing device when the fibre concentration in the image fall outside a selected range.

47. The apparatus according to claim 46, wherein the selected range is from 0 to 10 mm of the fibre per square mm of image.

48. The apparatus according to claim 30, wherein the image capturing device includes a recording device that can record images in a digital format.

49. The apparatus according to claim 44, wherein the image capturing device also includes an illuminating means to assist in the capture of images of the fibres.

50. The apparatus according to claim 49, wherein the illuminating means includes a light source positioned on the opposite side of the chamber to the recording device such that light transmitted through the fibres can be detected by the recording device.

51. The apparatus according to claim 50, wherein the illuminating means includes a light source on the same side of the chamber as the recording device such that light reflected from the fibres can be detected by the recording device.

52. The apparatus according to claim 49, wherein the illuminating means is moveable relative to the chamber such that when the image capturing means is moved relative to the chamber, the illuminating means is able to remain in a relatively fixed position compared to the image capturing device.

53. The apparatus according to claim 44, wherein the illuminating means is moveable by the drive assembly for moving the image capturing device.

* * * * *